United States Patent [19]

Zuckerman

[11] Patent Number: 5,223,227
[45] Date of Patent: Jun. 29, 1993

[54] DISPOSABLE PIN AND CUP WITH REUSEABLE STEM AND COLLAR FOR BLOOD COAGULATION ANALYZER

[75] Inventor: Leon Zuckerman, Skokie, Ill.

[73] Assignee: Haemoscope Corporation, Morton Grove, Ill.

[21] Appl. No.: 703,203

[22] Filed: May 20, 1991

Related U.S. Application Data

[63] Continuation of Ser. No. 367,853, Jun. 19, 1989, abandoned.

[51] Int. Cl.⁵ .................... G01N 11/10; G01N 33/16
[52] U.S. Cl. ..................... 422/102; 422/73; 422/103; 422/104; 73/59; 73/64.1; 73/64.42; 435/297
[58] Field of Search ............... 435/296, 297; 422/73, 422/99, 102, 103, 104; 73/64.1, 59

[56] References Cited

U.S. PATENT DOCUMENTS

| | | | |
|---|---|---|---|
| 3,865,551 | 2/1975 | Saiki et al. | 435/296 |
| 4,148,216 | 4/1979 | Do et al. | 73/59 |
| 4,317,363 | 2/1982 | Shen | 73/64.1 |
| 4,341,111 | 6/1982 | Husar | 73/64.1 |
| 4,524,610 | 6/1985 | Fitzgerald et al. | 73/54 |
| 4,551,308 | 11/1985 | Mintz | 422/58 |
| 4,592,226 | 6/1986 | Weber et al. | 73/59 |
| 5,016,469 | 5/1991 | Henderson | 73/64.1 |

FOREIGN PATENT DOCUMENTS 2370971 6/1978 France .

Primary Examiner—James C. Housel
Assistant Examiner—David Redding
Attorney, Agent, or Firm—Willian Brinks Olds Hofer Gilson & Lione

[57] ABSTRACT

An instrument for measuring the coagulation characteristics of whole blood samples is provided with disposable parts for contacting the blood. The pin has a blood-compatible plastic sleeve surrounding a metal stem which weights the pin assembly so it sinks into the blood sample. The metal stem also engages into the pin suspension apparatus of the instrument. A blood-compatible plastic cup receives the blood sample to be tested, and is surrounded by a metal collar to transfer heat to the cup for the time required for a test. The plastic surfaces which contact the blood sample are slightly roughened, to a matte finish, to improve adhesion so as to approximate the results obtained with stainless steel pins and cups.

12 Claims, 2 Drawing Sheets

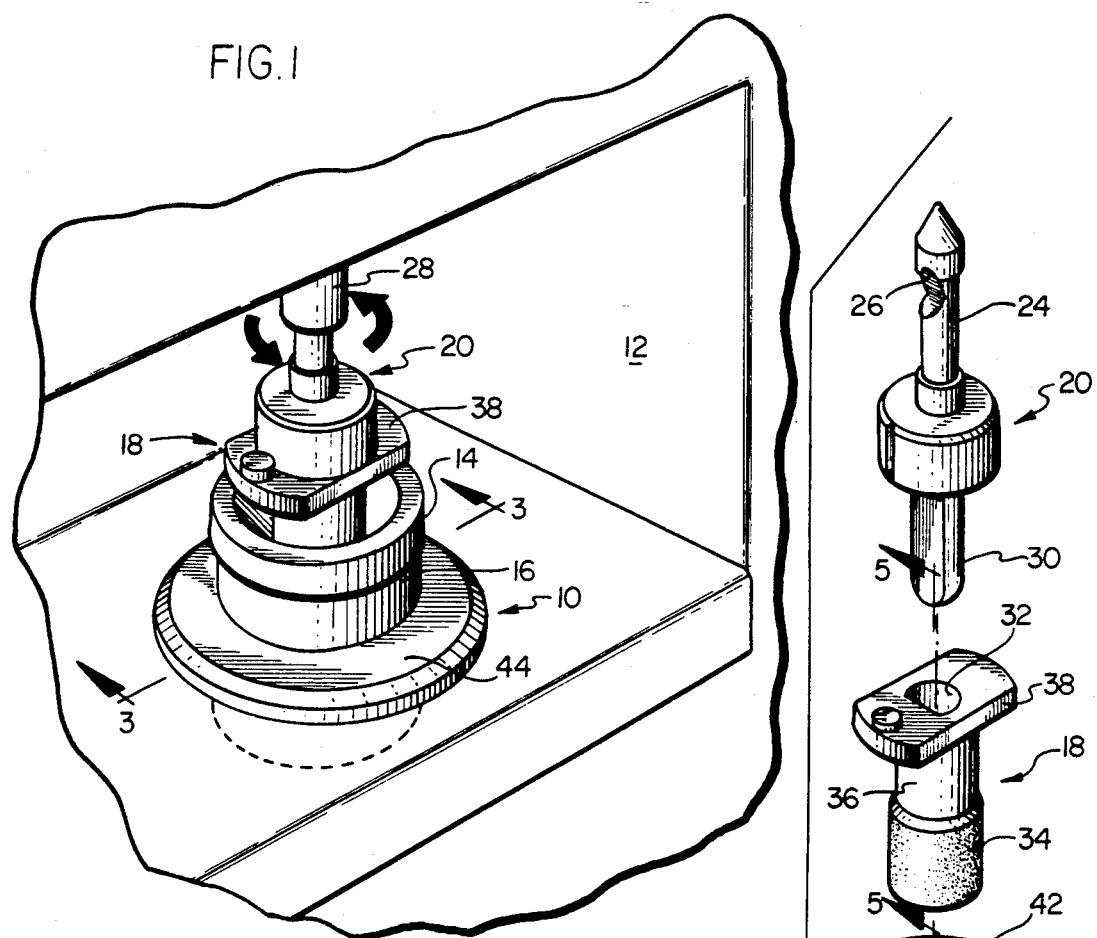
FIG.1
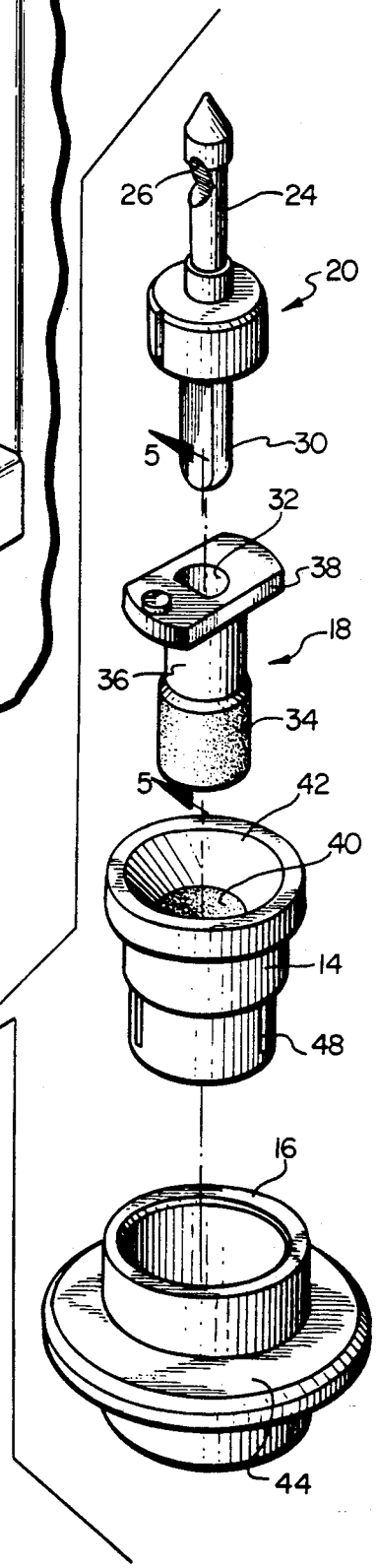
FIG.2
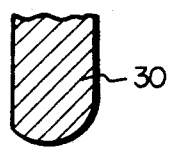
FIG.5
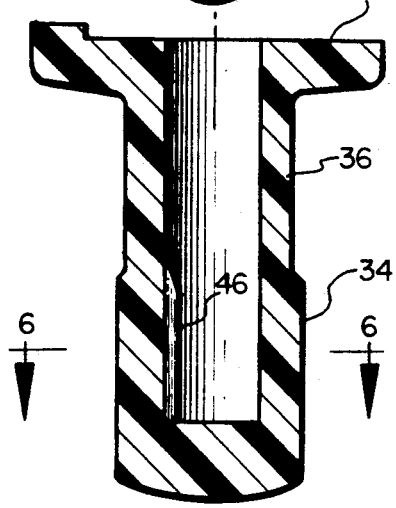

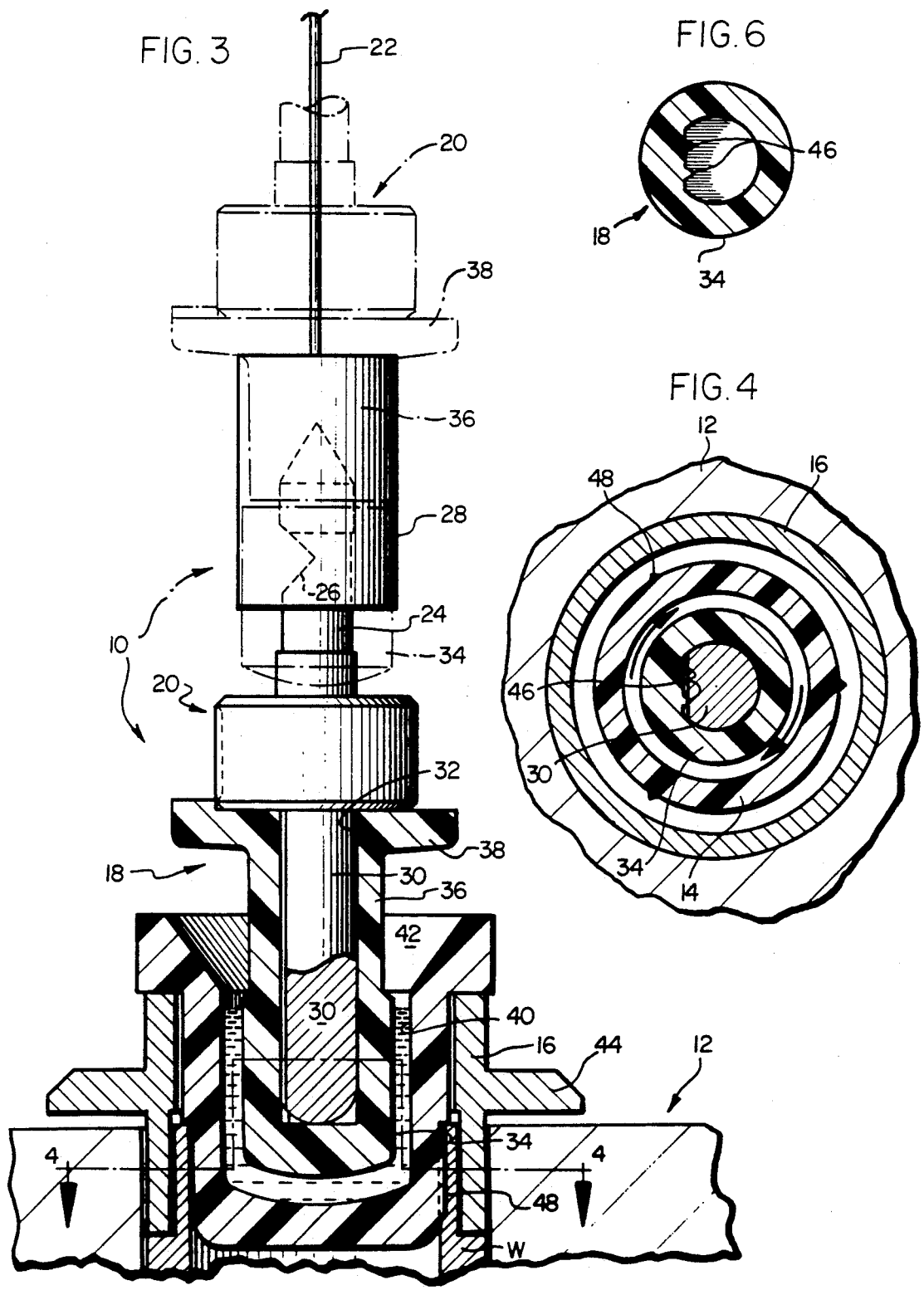

DISPOSABLE PIN AND CUP WITH REUSEABLE STEM AND COLLAR FOR BLOOD COAGULATION ANALYZER

REFERENCE TO PRIOR APPLICATION

This is a continuation of my prior application Ser. No. 367,853, filed Jun. 19, 1989, now abandoned.

FIELD OF THE INVENTION

The present invention relates to blood coagulation test instruments.

BACKGROUND OF THE INVENTION

Measurement of the ability of a patient's blood to coagulate in timely and effective fashion is crucial to certain surgical and medical procedures. Blood coagulation analyzer instruments have been known since Helmut Hartert developed them in Germany in the 1940's. A U.S. Pat. showing the background and continued development of the Hellige line of such instruments is No. 3,714,815.

In such instruments, a small stainless steel cup is prewarmed to body temperature. A sample of whole blood is placed into the cup. A cylindric pin suspended on a thin wire is lowered into the cup and the blood sample, which then is covered with mineral oil. The cup is oscillated gently, over about 10 seconds, back and forth through a small angle, about 4 degrees, around its vertical axis. As the blood coagulates or clots, elements in the blood link the cup and the pin surfaces together, so the pin too begins to oscillate. The oscillations of the pin are detected by reflected light beams, magnetically, or otherwise. Ultimately the pin and the cup oscillate together, if the clot is strong and does not break up.

Delay in onset of the clot, weakness of the clot, or breaking up of the clot are shown clearly in a real-time plot of the movements of the pin. The plot may be expressed by mathematical factors characterizing its shape.

Blood may be contaminated with hepatitis virus, AIDS virus, and other infectious agents dangerous to the personnel operating the blood test equipment. Cleaning of the surfaces contacting the blood necessarily brings such personnel into contact with the blood on the surfaces, particularly where the blood has congealed. Cleaning and drying must nonetheless be thorough, and the surfaces must not be scratched, to ensure accuracy of subsequent test results.

Although the desireability of use of disposable blood coagulation test implements has been recognized generally, no practicable structures for disposable pins and/or cups for use in blood coagulation test equipment have been proposed. Merely replicating the conventional stainless steel pins and cups in plastic does not overcome problems such as actually sinking the suspended pin in the blood, avoiding breakage of the thin shaft of the pin where it is inserted into the suspension and measuring assembly, and transferring adequate heat to the blood in the cup.

SUMMARY OF THE INVENTION

A pin and a cup for blood coagulation test instruments have blood-compatible plastic such as Cyro-G20 with slightly matte or roughened surfaces to contact the blood to be tested. The cup is formed of such plastic, with an axially-symmetric inner or side wall surface in the area contact the blood. Above the blood well the inner wall tapers sharply outwardly. A metal collar fits closely about the outside of the cup. The pin has a sleeve also formed of such plastic with an outer wall corresponding in size and shape to the inner wall of the cup, providing clearance for the blood. The sleeve thins in an upward area adjacent the tapered portion of the cup wall, and ends upwardly in a radially-extending head, to afford easier manipulation. The pin comprises also an inner metal stem having a lower end received snugly but removably in the plastic sleeve. An upper end of the stem is releasably engageable with the suspension and measuring apparatus of the test instrument. A central portion of the stem is enlarged to afford easier manipulation and to weight the pin so it will sink in the blood sample in the cup when suspended from a thin wire. The pin and cup of the invention are used in the same fashion and provide closely similar results as known stainless steel pins and cups, but after a test is conducted the used sleeve is quickly disconnected from the stem and discharged. The used cup is lifted from the metal collar and discarded. The stem and collar, never having touched blood, are easily and safely reused.

THE DRAWINGS

In the drawings:

FIG. 1 is a general perspective view of the pin and cup of the invention in use in the test area of a known blood coagulation test instrument;

FIG. 2 is an exploded perspective view of the pin and cup of the invention;

FIG. 3 is a longitudinal view, partly in section on line 3—3 of FIG. 1, through the cup and pin of the invention and the suspension apparatus, and showing a raised position of the pin in phantom;

FIG. 4 is an axial sectional view, on line 4—4 of FIG. 3, through the cup and pin of the invention;

FIG. 5 is a longitudinal sectional view, on line 5—5 of FIG. 4, through the sleeve and stem of the pin of the invention; and FIG. 6 is an axial sectional view, on line 6—6 of FIG. 5, through the sleeve of the invention.

DESCRIPTION OF THE PREFERRED EMBODIMENT

A disposable pin and cup assembly 10 according to one form of the invention is shown in FIG. 1 in use during a blood coagulation test in a test instrument 12 such as a Hellige THROMBELASTOGRAPH D instrument. The test instrument includes oscillation means, not shown, for holding and gently oscillating a cup 14 containing a blood sample to be tested through a small arc, about 4 degrees 45 minutes of arc, with each oscillation (back and forth) being completed in about 10 seconds. A metal collar 16 fits closely about the cup 14 and helps to maintain the desired temperature of the blood.

A pin comprising a plastic sleeve 18 and a metal stem 20 is suspended from a thin wire 22 in the instrument 12, as shown in FIG. 3. The stem 20 is formed with an upper engagement portion 24 including an alignment notch 26, which removably engages into a receptacle 28 affixed to the wire 22. The stem also has a lower portion 30 which is removably inserted into a central axial opening 32 of the sleeve 18. A center portion of the stem 20 is enlarged as shown to add weight to the pin assembly to sink same into the blood, to allow easier manipulation, and to provide a stop surface for the sleeve 18.

The sleeve 18 is formed of a blood-compatible acrylic plastic such as Cyro-G20. It has an axially-symmetric, slightly roughened or matte-finish outer test surface 34 extending for a distance above its lowermost point as shown in FIGS. 2, 3, and 5, with a reduced-diameter portion 36 above that, and then a radially-extending head 38 at the top. The top of the head 38 contacts the enlarged center portion of the stem to ensure proper seating of the sleeve on the stem and to ease manipulation.

The cup 14 is also formed of a blood-compatible plastic such as Cyro-G20. The cup has an inner wall 40 corresponding in size and shape to the outer surface 34 of the sleeve 18. The inner wall 40 is also axially-symmetric, and extends a distance above its bottom about equal to that of the sleeve surface 34. It has a slightly roughened or matte finish. The inner surface of the cup 14 then tapers outwardly quickly near the top of the cup, as at surface 42, to accommodate excess oil or blood placed into the cup without affecting test results.

The blood-contacting surfaces 34 and 40 are formed with a slight roughness or matte finish, which is imparted by sand-blasting the corresponding surfaces of stainless steel forming or casting molds. Tested by ANSI No. B46.1 (1978), the sleeve surface 34 has a roughness of 4.0 to 9.9 microinches and the cup inner surface 40 has a roughness of 17.7 to 33.5 microinches in representative samples. The roughness enhances the adhesion of clots of blood to the plastic and provides results using the plastic parts to be closely similar to results obtained using conventional stainless steel pins and cups.

An outer wall of the cup 14 is formed to fit closely into the metal collar 16, but with some clearance. A lower part of the cup is snugly received in a well W, which is heated and which oscillates within the instrument 12, so the cup will oscillate with the collar in the test station of instrument 12.

The collar 16 is formed of a heat-conductive metal such as aluminum, to conduct heat from the test station 12 through the plastic cup 14 to the blood in the cup throughout the test procedure. A wide flange 44 on the outside of the collar is slightly elevated above the surfaces of the test station 12, to facilitate removal of the collar and cup.

At least one internal surface of the sleeve 18 which engages a metal surface of the stem 20 is formed with integrally molded crush lines or projections 46 as shown in FIGS. 4, 5, and 6. These crush lines ensure the tightness of fit between the stem and the sleeve, to ensure reproducable test results. Similar projections 48 are provided on well W and the outside of the cup 14 to insure firm contact with the cup drive mechanism (not shown).

In use, the collar 16 and cup 14 are pre-warmed to body temperature by test station area 12, which is also heated to maintain the blood sample's temperature during the 20-40 minute test. The collar 16 insures even heating of all of the cup 14. The stem 20 and sleeve 18 are assembled together by inserting the lower portion 30 of the stem into the central axial hollow 32 of the sleeve. The upper portion 24 of the stem is aligned and engaged at its notch 26 with the receptacle 28 of the test instrument 12. A sample of whole blood to be tested is placed in the plastic cup 14 surrounded by the metal collar 16 in the test station of the instrument 12. The wire 22 and pin assembly are then lowered into the test position, with the lower surface 34 of the sleeve 18 immersed in the blood within cup 14. A thin film of mineral oil is applied to the surface of the blood, about the pin, to reduce contact of the blood with air. The oscillation of well W is started, and recording of the oscillation of the pin assembly induced by clotting of the blood sample is shown or measured and recorded on an output device (not shown).

To remove the pin and cup from the test instrument 12, the pin is raised in the machine. The stem and sleeve are pulled downward from the receptacle and placed back into the cup. The whole pin, cup, and collar assembly is next lifted and removed from the test instrument. The stem and sleeve are separated by prying them apart between the enlarged stem center portion and the head of the sleeve, and the cup and sleeve are discarded. The stem and collar are then reused with new plastic parts.

Other forms of blood coagulation test equipment may be used with the disposable pin and cup of the invention, to good advantage. If the pin is rotated, or if other forms of measurement are used, the parts may be adapted accordingly and the same advantages obtained.

The present invention is disclosed in a preferred form as presently known and practiced. Other forms of the invention may readily be devised to vary and to improve the application of same in different environments or uses. The present invention is not solely defined or limited by what is specifically shown or described herein, but is indicated in the appended claims.

I claim as my invention:

1. Apparatus for use in a blood coagulation analyzer, the apparatus comprising:
   a metal stem having an end portion, the stem constructed so as to releasably and non-rotatably engage a sleeve at said end portion;
   the sleeve having first and second opposite end portions, the first end portion constructed so as to releasably engage the end portion of the stem, the sleeve being further constructed so as to define an external surface extending between said first and second opposite ends, and at least a portion of said external surface being axially-symmetric and comprising a roughened surface, wherein the roughness of said external surface of the sleeve measures above about 4 microinches; and
   a cup having opposite first and second ends, the cup defining an opening at said first end and closed at its second end, said opening in said cup defining an internal surface, at least a portion of said internal surface defining a roughened portion, wherein the roughness of said roughened portion of the cup measures above about 4 microinches, and said roughened surface of said sleeve being received in said roughened portion of said cup.

2. An apparatus as defined in claim 1, wherein the sleeve and the cup are formed of acrylic plastic.

3. An apparatus as defined in claim 1, wherein the first end portion of the sleeve is constructed so as to have an opening and a deformable member therein, the deformable member tightly engaging the end portion of the stem into said opening.

4. An apparatus as defined in claim 1, wherein the roughened portion and surface are generally cylindrical.

5. An apparatus as defined in claim 1, wherein the sleeve has an enlarged, radially-extending head, said head being spaced from the roughened external surface and extending to about said first end portion thereof.

6. An apparatus as defined in claim 1, further comprising a metal collar having an end portion, the end portion being constructed so as to receive said second end of said cup.

7. An apparatus as defined in claim 6, wherein the cup is constructed with an outside portion and at least one deformable member on said outside portion so as to tightly engage said collar.

8. An apparatus as defined in claim 1, wherein the roughness of the external surface of the sleeve measures about 4 to about 34 microinches.

9. An apparatus as defined in claim 1, wherein the roughness of the roughened portion of the cup measures about 4 to about 34 microinches.

10. An apparatus as defined in claim 1, wherein the roughness of the external surface of the sleeve and of the roughened portion of the cup each measures about 4 to about 34 microinches.

11. An apparatus as defined in claim 1, wherein the roughness of the external surface of the sleeve measures about 4 to about 10 microinches and the roughness of the roughened portion of the cup measures about 17 to about 34 microinches.

12. An apparatus as defined in claim 1, wherein the stem and sleeve are of a weight and density such that the stem and sleeve do not float but sink in the cup by their own weight in a blood sample therein.

* * * * *

UNITED STATES PATENT AND TRADEMARK OFFICE
CERTIFICATE OF CORRECTION

PATENT NO. : 5,223,227
DATED : June 29, 1993
INVENTOR(S) : Leon Zuckerman

Page 1 of 2

It is certified that error appears in the above-indentified patent and that said Letters Patent is hereby corrected as shown below:

On the title page, item [54], and column 1, in the title: "REUSEABLE" and substitute therefor --REUSABLE--.

In column 1, line 68, delete "contact" and substitute therefor --contacting--.

In column 2, lines 8 & 9, delete "pin comprises also" and substitute therefor --pin also comprises--.

In column 2, line 11, delete "engageable" and substitute therefor --engaged--.

In column 2, line 20, delete "discharged" and substitute therefor --discarded--.

In column 2, line 24, before "THE DRAWINGS" insert "BRIEF DESCRIPTION OF".

UNITED STATES PATENT AND TRADEMARK OFFICE
CERTIFICATE OF CORRECTION

PATENT NO. : 5,223,227
DATED : June 29, 1993
INVENTOR(S) : Leon Zuckerman

It is certified that error appears in the above-indentified patent and that said Letters Patent is hereby corrected as shown below:

Column 4, claim 3, line 5, before "into" insert --inserted--.

Signed and Sealed this

First Day of November, 1994

Attest:

BRUCE LEHMAN

Attesting Officer      Commissioner of Patents and Trademarks